(12) United States Patent
Tremblay et al.

(10) Patent No.: US 10,398,838 B2
(45) Date of Patent: Sep. 3, 2019

(54) AUTO-INJECTOR (71) Applicant: DUOJECT MEDICAL SYSTEMS INC., Bromont, Quebec (CA)

(72) Inventors: Yan Tremblay, Orford (CA); Sylvain Cloutier, Magog (CA); Simon Hamel, Sutton (CA)

(73) Assignee: Duoject Medical Systems Inc., Bromont, Quebec (CA)

( * ) Notice: Subject to any disclaimer, the term of this patent is extended or adjusted under 35 U.S.C. 154(b) by 274 days.

(21) Appl. No.: 14/392,399

(22) PCT Filed: Nov. 17, 2014

(86) PCT No.: PCT/CA2014/000837
§ 371 (c)(1),
(2) Date: May 6, 2016

(87) PCT Pub. No.: WO2015/070340
PCT Pub. Date: May 21, 2015

(65) Prior Publication Data
US 2016/0287788 A1    Oct. 6, 2016

(51) Int. Cl.
*A61M 5/20* (2006.01)
*A61M 5/32* (2006.01)
(Continued)

(52) U.S. Cl.
CPC ............ *A61M 5/2033* (2013.01); *A61M 5/24* (2013.01); *A61M 5/31576* (2013.01); *A61M 5/3202* (2013.01); *A61M 5/326* (2013.01); *A61M 5/002* (2013.01); *A61M 2005/206* (2013.01); *A61M 2005/208* (2013.01); *A61M 2005/247* (2013.01);
(Continued)

(58) Field of Classification Search
CPC .. A61M 5/2033; A61M 5/24; A61M 5/31576; A61M 5/3202; A61M 2005/2026; A61M 2005/208; A61M 2005/2073; A61M 2005/206; A61M 2005/247
See application file for complete search history.

(56) References Cited

U.S. PATENT DOCUMENTS

| | | | | |
|---|---|---|---|---|
| 2002/0183690 A1* | 12/2002 | Arnisolle | ............ | A61M 5/2066 604/83 |
| 2006/0229570 A1* | 10/2006 | Lovell | ..................... | A61M 5/20 604/218 |
| 2010/0211005 A1* | 8/2010 | Edwards | ............... | A61M 5/002 604/82 |

FOREIGN PATENT DOCUMENTS

WO    WO-2012143440 A1 * 10/2012 .......... A61M 5/2448

\* cited by examiner

*Primary Examiner* — Kevin C Sirmons
*Assistant Examiner* — Leah J Swanson
(74) *Attorney, Agent, or Firm* — Eric Fincham (57) ABSTRACT

An auto-injector pen has an outer housing (12, 14) which has a proximal end (18) and a distal end (16), an inner housing (84) having a cartridge (74) therein, the cartridge (74) containing a medicament and having one end thereof sealed by pierceable member (80), a needle hub (64) having first and second piercing tips (68, 70) which are in fluid communication, an actuating assembly (28) which moves an actuator from a first position to an activated position wherein the first piercing tip (68) extends outwardly of the outer housing (12,14) at the proximal end (18) and the second piercing tip (70) pierces the pierceable member (80), a first trigger (22) located at the distal end (16) and a second trigger (98) located at proximal end 18, the arrangement being such that the second trigger 98 must be activated to permit activation of the first trigger (22).

8 Claims, 15 Drawing Sheets

(51) Int. Cl.
*A61M 5/315* (2006.01)
*A61M 5/24* (2006.01)
*A61M 5/00* (2006.01)

(52) U.S. Cl.
CPC ............. *A61M 2005/31588* (2013.01); *A61M 2202/048* (2013.01); *A61M 2205/3553* (2013.01); *A61M 2205/50* (2013.01); *A61M 2205/8206* (2013.01)

AUTO-INJECTOR

FIELD OF THE INVENTION

The present invention relates to a medical device and more particularly, relates to a delivery device known as an auto-injector for injecting a medicament into the body of a patient.

BACKGROUND OF THE INVENTION

Auto-injectors are well known in the art and, as aforementioned, are used to inject a medicament into the body of a patient. The injection is usually done by the patient. Certain allergic reactions such as exposure to peanuts, shellfish, certain drugs, toxins and the like can result in an allergic reaction in some individuals. Typically, the allergic reaction will lead to anaphylactic shock which results in a sharp drop in blood pressure. Other reactions such as airway constriction can also occur.

In order to respond to such a reaction, an individual can carry an auto-injector to administer an injection of a substance which can provide relief from the allergic reaction. Typically, such an injection is of Epinephrin (adrenaline). As aforementioned, auto-injectors are known in the art and come in different configurations. Typically, the user is supposed to place a first end against a body surface (typically a thigh) and then a trigger is activated to commence the injection process. However, given the condition of the user at the time, confusion can result in the user putting the wrong end against the thigh. This may result in the user actuating the auto-injector away from the intended injection sight. Naturally, this is highly undesirable since the user typically only carries a single dose and unless other sources are available, the allergic reaction will not be treated.

SUMMARY OF THE INVENTION

It is therefore an object of the present invention to provide for an auto-injector which will result in consistent and reliable activation of the auto-injector.

According to one aspect of the present invention, there is provided an auto-injector comprising an outer housing having a proximal and a distal end, an inner housing, a cartridge located within the inner housing, the cartridge containing a medicament, the cartridge having one end thereof sealed by a pierceable member, a needle hub, the needle hub having first and second piercing tips, the first and second piercing tips being in fluid communication, an actuating assembly, the actuating assembly being arranged to move an actuator from a first storage position to an activated position wherein the first piercing tip extends outwardly of the outer housing at the proximal end and the second piercing tip pierces the pierceable member, a first trigger being located at the distal end, the trigger being operative to the to cause activation of the actuating assembly, and a second trigger being located at the proximal end, the arrangement being such that the second trigger must be activated to permit activation of the first trigger.

The outer housing is preferably formed of two pieces secured to each other. The means of securement may be any typical such as by the use of clips and/or fastening devices such as screws.

The cartridge can be selected from those known in the art. The cartridge is typically an elongated vessel containing a medicament. The medicament is contained within the cartridge by having at least one end thereof sealed by a pierceable member. The pierceable member may comprise the cap of the cartridge or alternatively, could comprise a plunger sealing the internal cavity. For the practice of the present invention, it is preferred that the cap be the one provided with the pierceable member.

The needle preferably carries a staked-in needle which will have first and second piercing tips as is known in the art. The first and second piercing tips are in fluid communication which is necessary such that the medicament may flow from the cartridge to the injection site.

The actuating assembly preferably comprises upper and lower members. The term "upper" and "lower" are relative and in the instant application, the word upper refers to the part of the actuating assembly closest to the distal end of the auto-injector. Conversely, the term "lower" refers to that portion of the actuating assembly which is closer to the proximal end of the auto-injector.

The actuating assembly secures the upper portion and lower portion together with compressed springs being mounted therebetween. A trigger mounted at the distal end is designed to release the lower member from the upper member. The springs are utilized to drive the lower portion with a force sufficient to cause the needle to extend outwardly of the outer housing and the cartridge to be pierced by the needle.

As aforementioned, there is a first trigger which is located at the distal end while there is a second trigger located at the proximal end. The arrangement is such that only upon activation of the second trigger by the patient or user pressing the auto-injector against the site to be injected, will cause the actuating assembly to move to a position where it can be actuated by the first trigger.

Following activation, the needle hub will be returned to a position such that the needle no longer projects outwardly of the outer housing.

The auto-injector is preferably provided with a circuit board and battery. Many different features can be built in. Thus, one of the major problems with auto-injectors is the patient requiring use of the same may tend to forget to carry the auto-injector at all times. In order to overcome this, the auto-injector could be electronically linked to a cell phone of the user. Once a certain distance exists between the telephone and the auto-injector, a reminder is given to the user that the auto-injector is not present. The reminder may be any suitable including auditory or visual.

Other features could include an arrangement that once it has been activated, it will notify one or more sites that it has been used. This can be used, in conjunction with GPS capabilities to locate the use and ensure that the patient is not in distress. For example, the device could have the capability of sending a message to a Doctor or other medical centre advising that it has been used.

The device could also be used to monitor the exposure of the device to ambient conditions. This can be important with certain medications which are sensitive to heat. If the device is exposed to sufficient heat for a certain of time, a message could be sent advising that the medication may have been comprised. This could be used to automatically forward a replacement device to the user.

Similarly, the device could also be programmed to automatically reorder when the expiration date is reached.

Still further, if for some reason, a second injection is required, the capability of locating other devices in the immediate area could be programmed.

The arrangement of signalling with the device has been used could be easily built into the device. Thus, two metallic contacts could be in a normally separated position prior to activation. Once the actuating assembly has been moved, this could permit the two electrical contacts to contact each other and thereby send a signal.

BRIEF DESCRIPTION OF THE DRAWINGS

Having thus generally described the invention, reference will be made to the accompanying drawings illustrating an embodiment thereof, in which.

DETAILED DESCRIPTION OF THE INVENTION

Referring to the drawings in greater details and by reference characters thereto, there is illustrated an auto-injector generally designated by reference numeral 10. Auto-injector 10 is designed to inject or administer an injection of a substance.

Auto-injector 10 has an outer housing characterized by a first half outer housing 12 and a second half outer housing 14. For the purposes of this disclosure, Applicant will refer to a distal end generally designated by reference numeral 16 and a proximal end generally designated by reference numeral 18. As used herein, the term "distal end" refers to the end remote from the injection site while the term "proximal end" refers to the end closest to the injection site.

At distal end 16, there is provided a trigger 22 in the form of a push button. Mounted immediately below and somewhat within trigger 22 is a battery 24 and a printed circuit board 26. Printed circuit board 26 is used to control the electronic functions of the device as will discussed hereinbelow. A spring 34 biases said trigger 22. A pair of metallic contacts 29 extend downwardly from printed circuit board 26. They are separated prior to activation.

Auto-injector 10 includes an actuating assembly generally designated by reference numeral 28. Actuating assembly 28 includes an upper member generally designated by reference numeral 30 and a lower member generally designated by reference numeral 32.

Upper member 30 has a recessed top surface 36 having a plurality of apertures 38 formed therein. There are four such apertures 38. On either side, there are provided a pair of ears 40 each having a passageway generally designated by reference numeral 42 extending therethrough.

Lower member 32 includes a base 46 with a pair of upwardly extending side walls 48, 50. On a first side, there is provided a pair of legs 52 which are slightly spaced apart and have tabs 54 at an upper end thereof. Similarly, there are provided legs 56 on the opposite side with each having tabs 58 formed thereon. A pair of compressed springs 44 extend about legs 52, 56 between lower member 32 and upper member 30. A recess 31 is provided at the upper edge.

Situated between upper member 30 and lower member 32 is a movable plunger 60 having diamond shaped protrusions 62 on either thereof. Protrusions 62 fit within recess 31.

A needle hub 64 has a staked in needle 66 with a first piercing tip 68 and a second piercing tip 70. A cartridge 74 contains a medicament 78. Cartridge 74 has a plunger 76 within its body and a pierceable top 80.

Auto-injector 10 has an inner housing 84. Inner housing 84 has a cylindrical base 86 with protrusions 88 located thereon. Above protrusions 88, there is provided a circular stopper flange 90. The upper portion of inner housing 84 includes slots 92 to thereby divide the inner housing 84 into leg-like structures. At the upper portion of inner housing 84, there are provided tabs 94 which are designed to engage with top surface 36 of upper member 30 to thereby retain inner housing 84 in position.

At its proximal end 18, auto-injector 10 is provided with a trigger 98. Trigger 98 has a bottom wall 100 with an aperture 102 formed therein to permit staked-in needle 68 to extend outwardly therefrom. Trigger 98 also has a front wall 104 and a back wall 106. Tabs 108 extend upwardly therefrom. There are also provided inverted U-shaped members 110 which are designed to engage with protrusions 88 of inner housing 84 to thereby interconnect the two members. A housing 114 has a flange 116 with a coil spring 112 which extends between trigger 98 and needle hub 64 over housing 114.

A cover 126 is designed to extend about trigger 98. Cover 126 is removable when use of auto-injector 10 is required.

Figure 1:
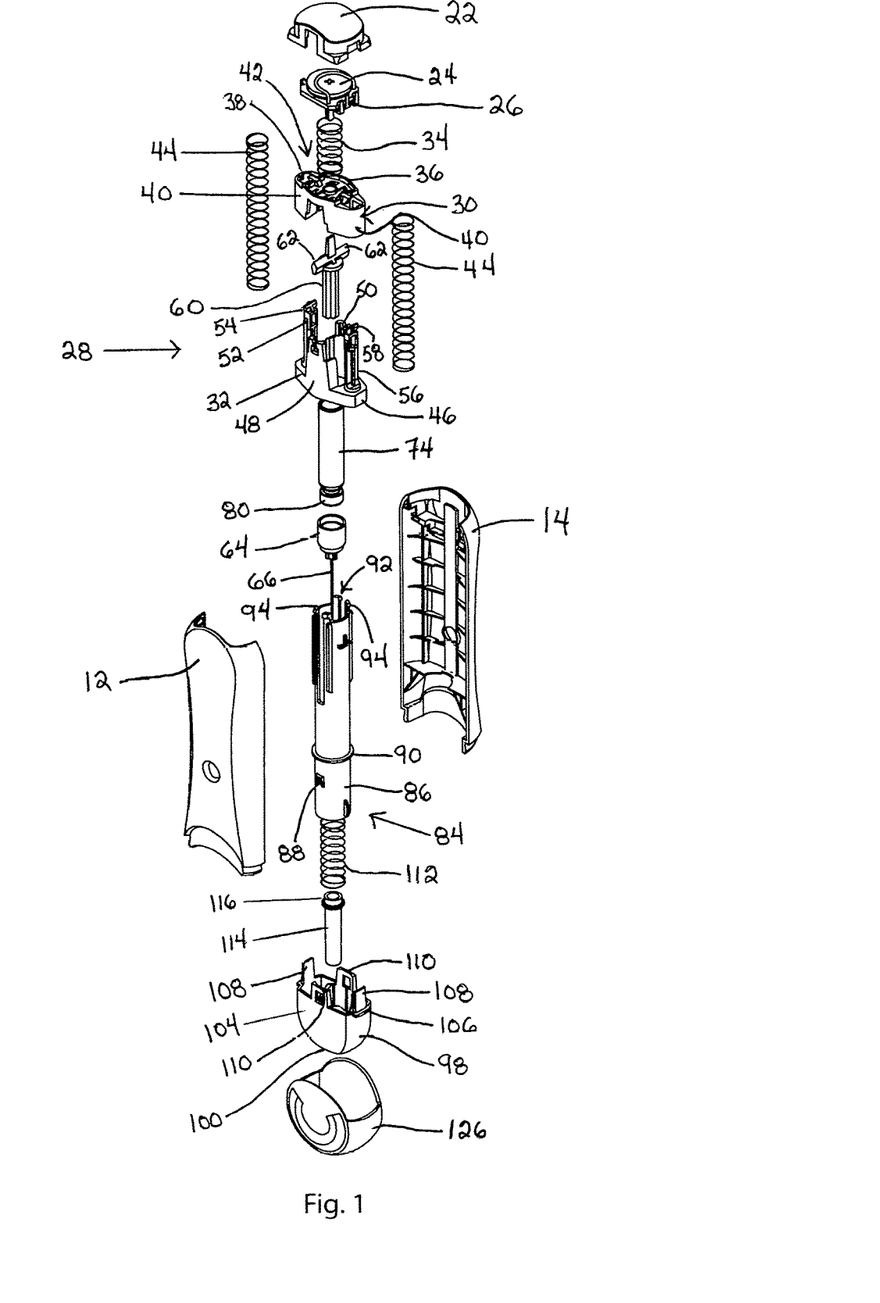
FIG. 1 is an exploded view of the auto-injector of the present invention.
Figure 2:
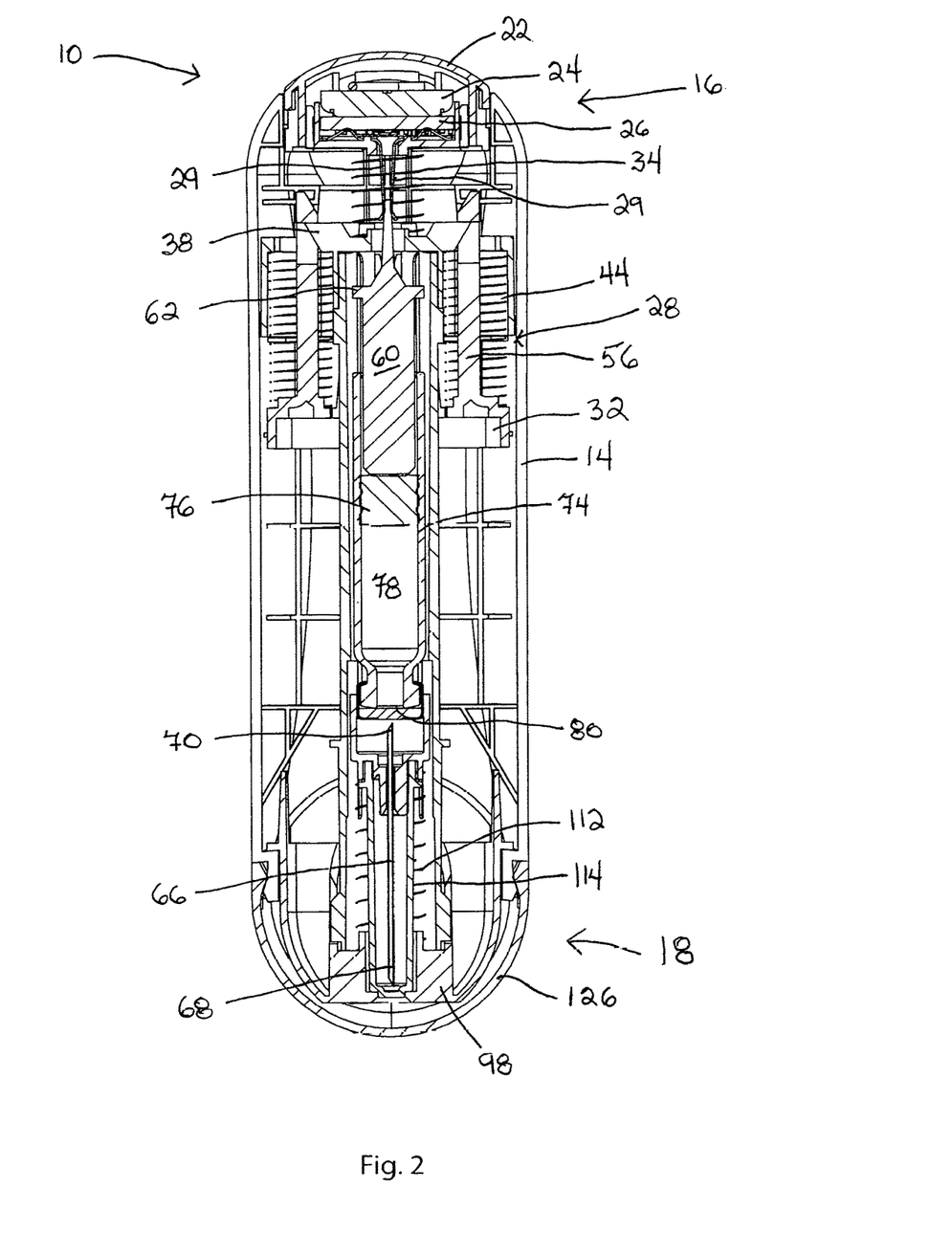
FIG. 2 is a sectional view of the auto-injector when in a stored position.
Figure 3:
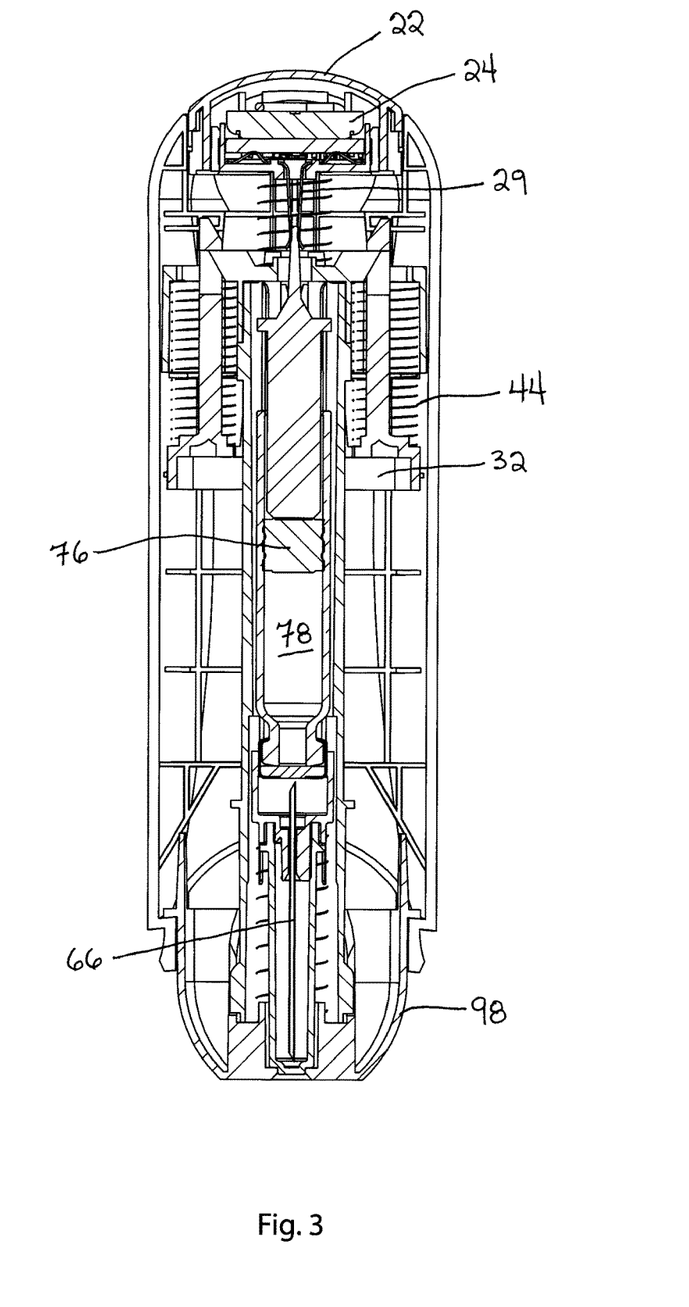
FIG. 3 is a sectional view illustrating removal of the cap.
Figure 4:
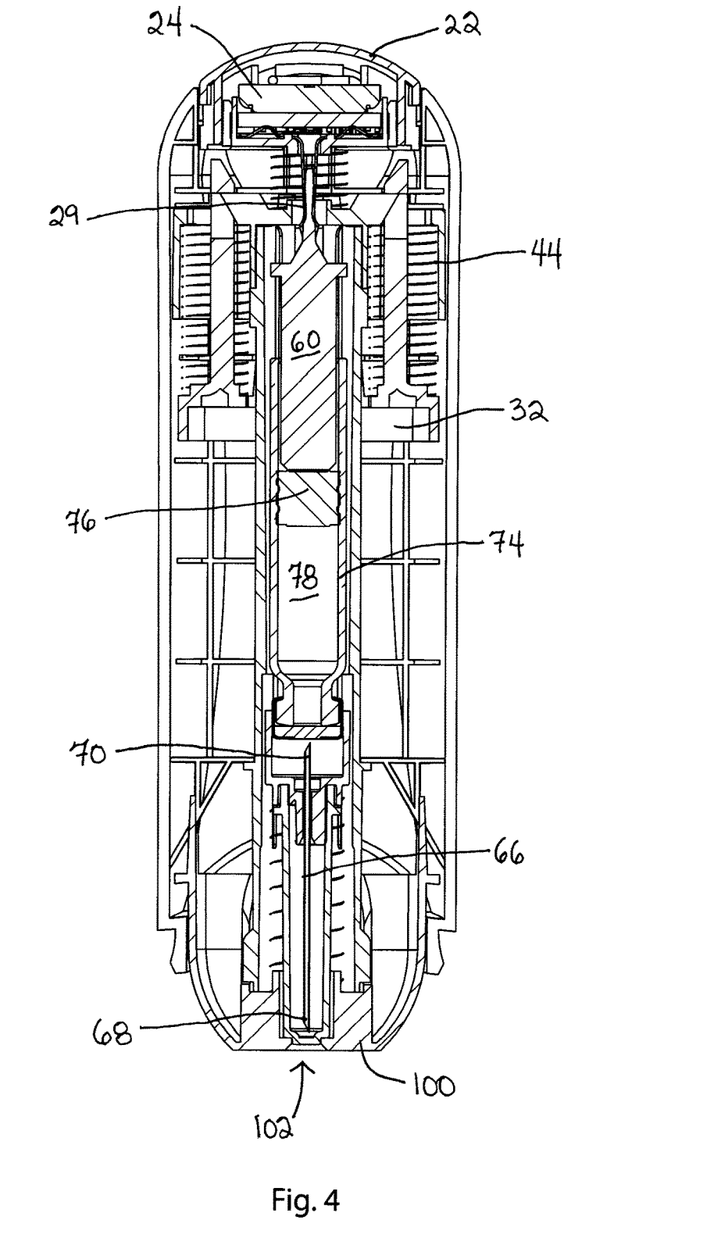
FIG. 4 is a sectional view illustrating commencement of the pressing of the second trigger.
Figure 5:
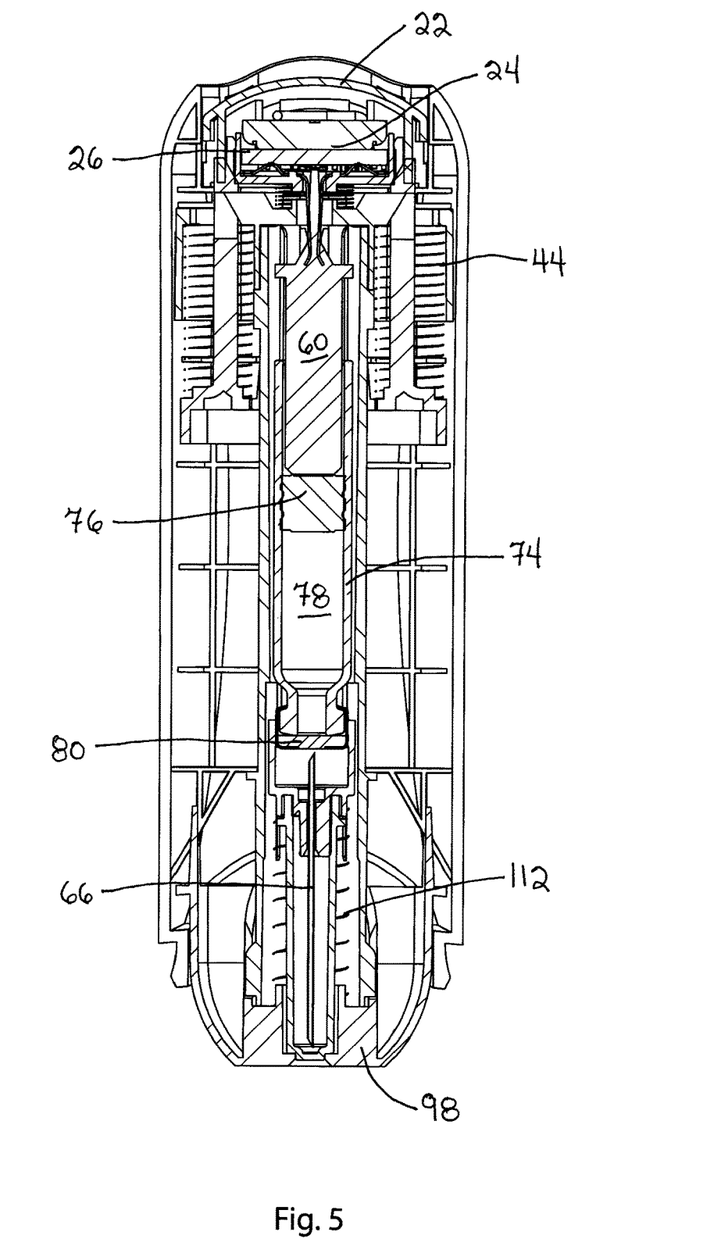
FIG. 5 is a sectional view illustrating commencement of the activation of the first trigger.
Figure 6:
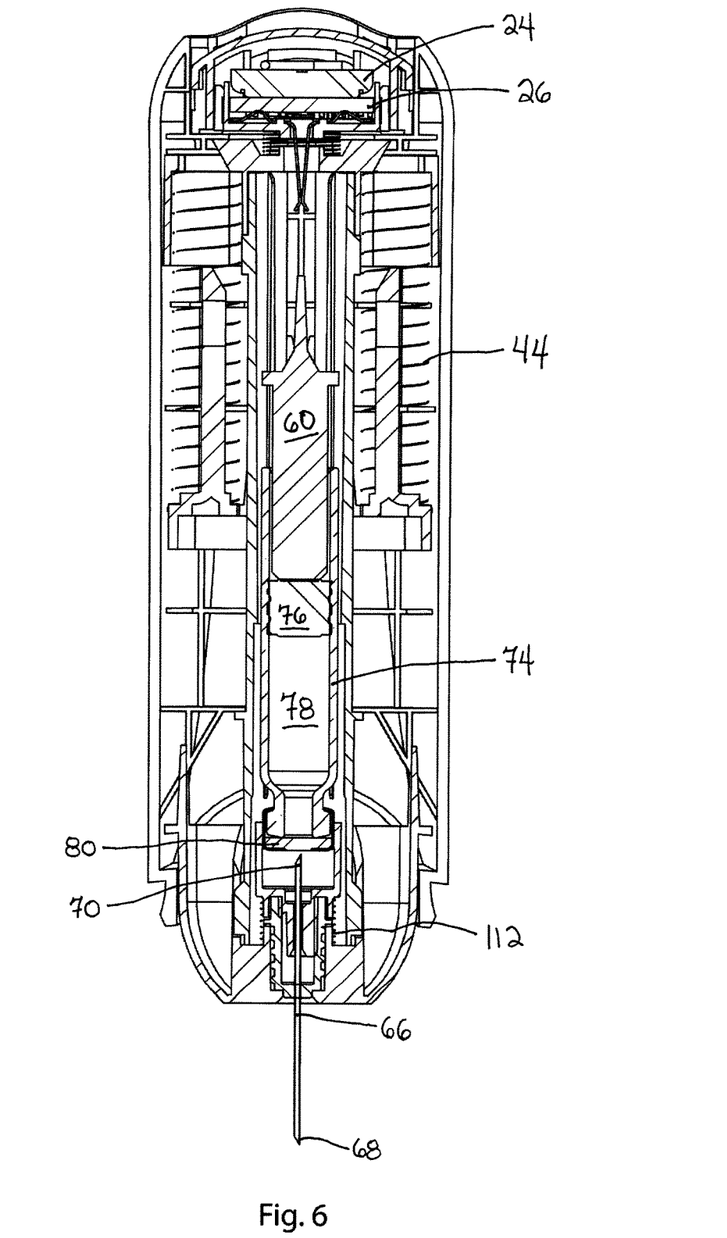
FIG. 6 is a sectional view illustrating the auto-injector during activation.
Figure 7:
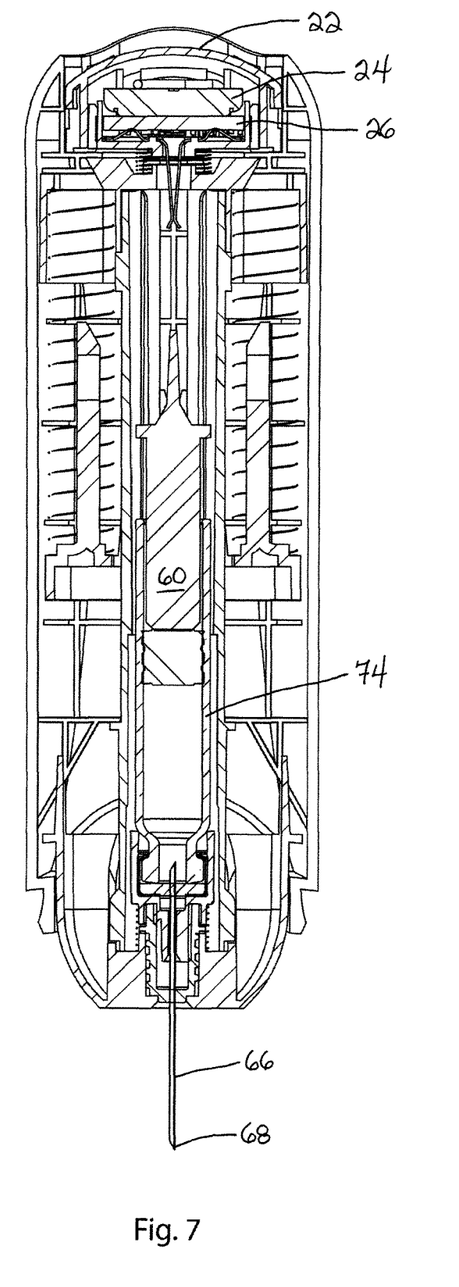
FIG. 7 is a sectional view illustrating the auto-injector fully activated.
Figure 8:
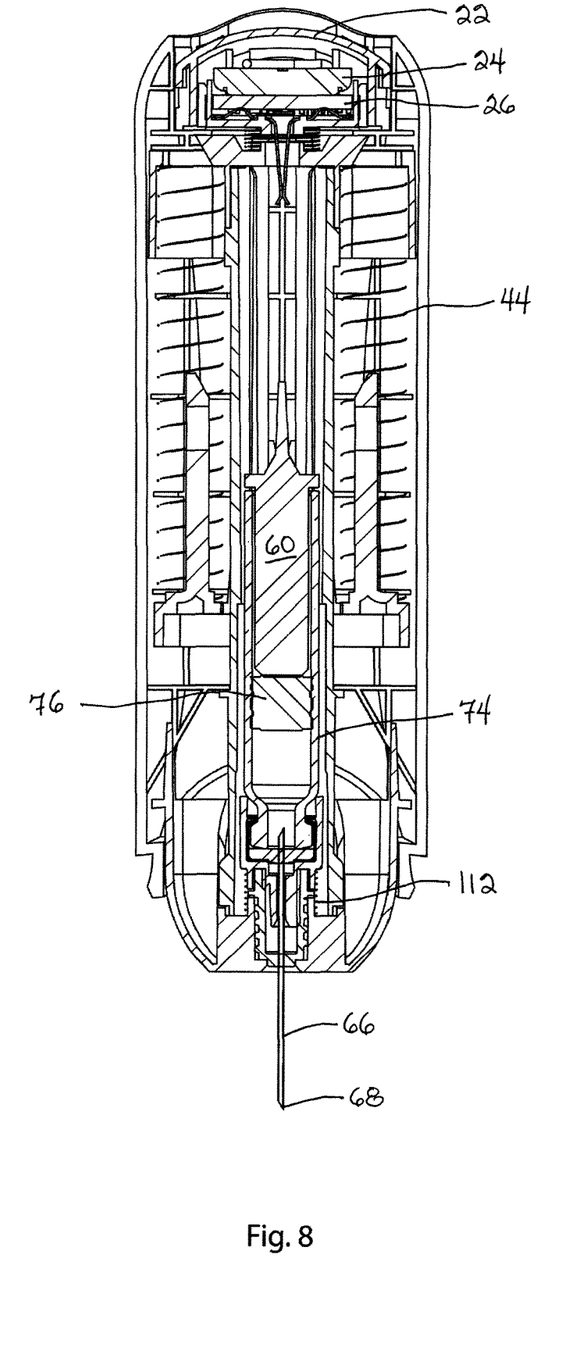
FIG. 8 is a sectional view illustrating the auto-injector at the end of activation.
Figure 9:
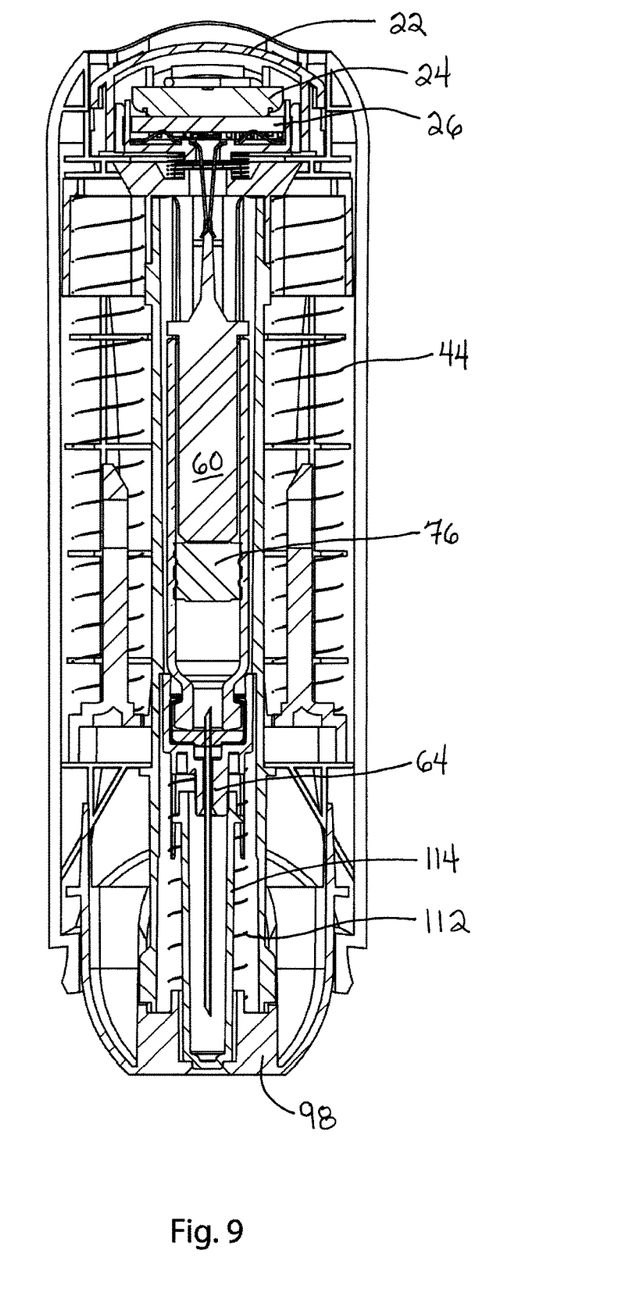
FIG. 9 is a sectional view illustrating retraction of the needle.
Figure 10:
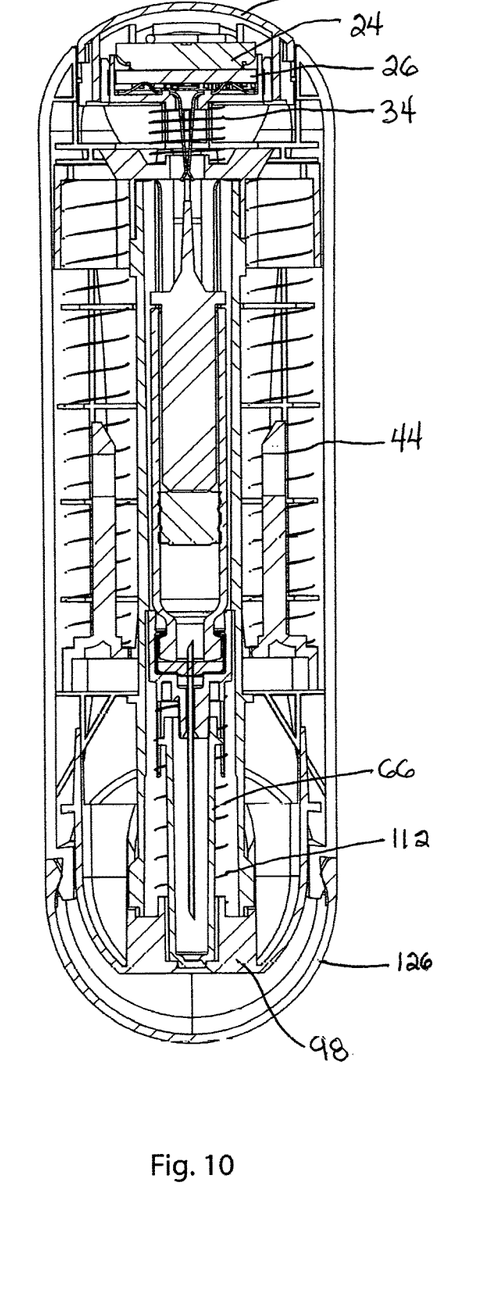
FIG. 10 is a sectional view illustrating the spent auto-injector with the cover replaced.
Figure 11:
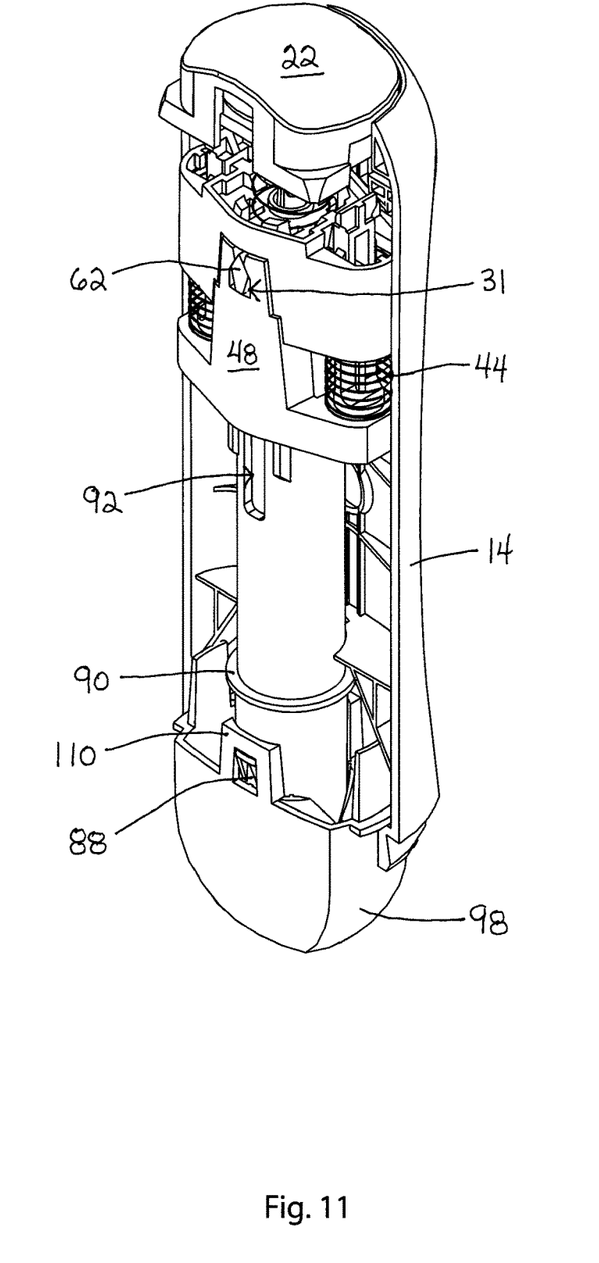
FIG. 11 is a perspective cutaway view of the auto-injector when in the position shown in FIG. 3.
Figure 12:
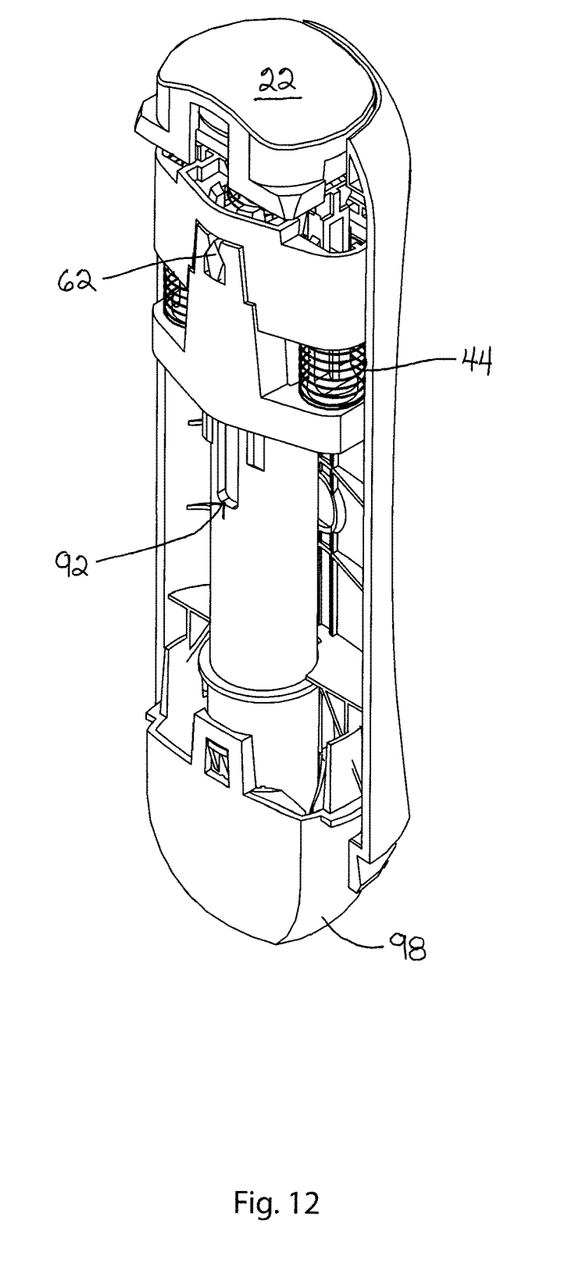
FIG. 12 is a perspective cutaway view of the auto-injector in the position illustrated in FIG. 4.
Figure 13:
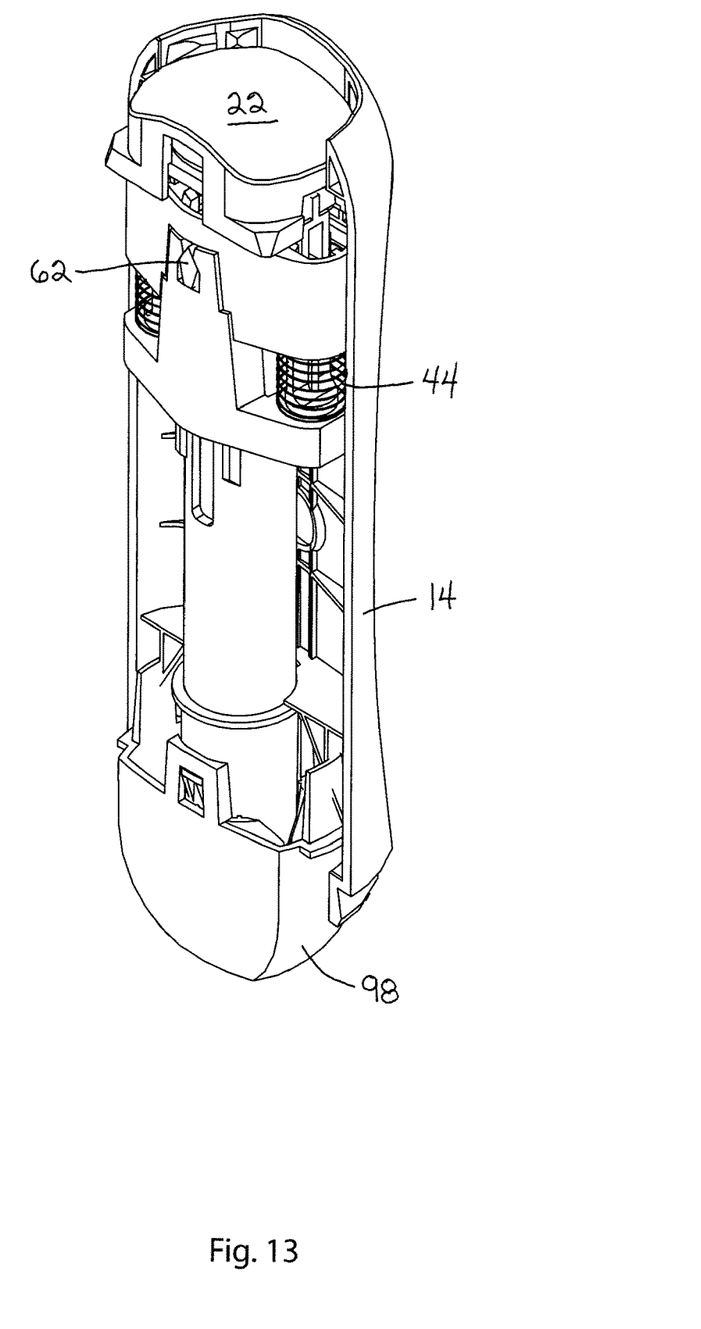
FIG. 13 is a perspective cutaway view of the auto-injector in the position illustrated in FIG. 5.
Figure 14:
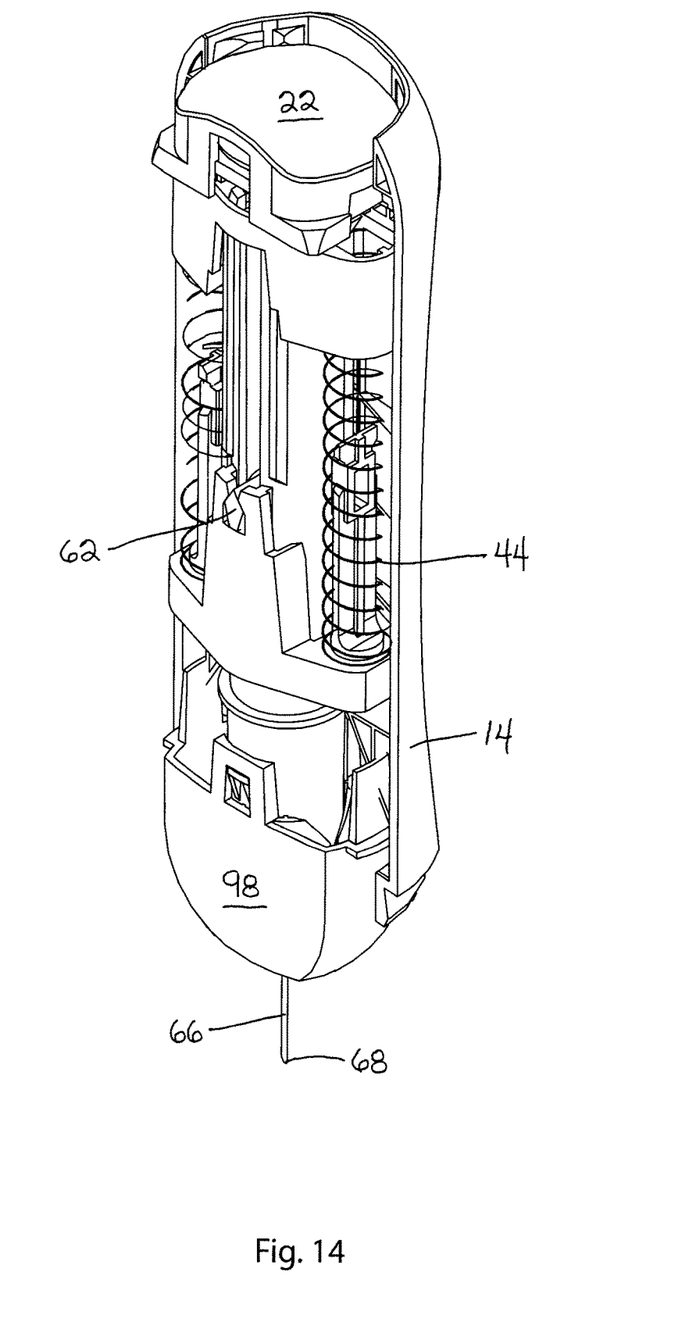
FIG. 14 is a perspective cutaway view of the auto-injector when in the position shown in FIG. 6.
Figure 15:
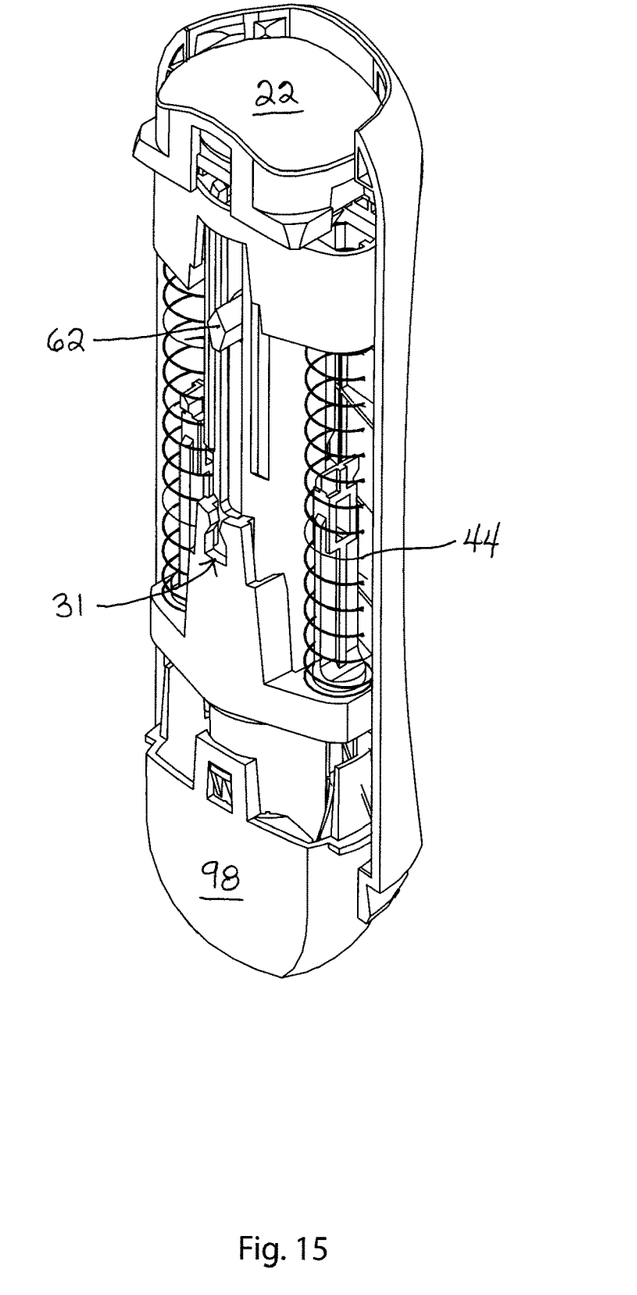
FIG. 15 is a perspective cutaway view of the auto-injector when in the position illustrated in FIG. 7.

In operation, in order to initiate activation, auto-injector 10 is pressed such that trigger 98 is against the body surface where the injection is to take place. Pressing of trigger 98 will cause actuating assembly 28 to move upwardly. This places actuating assembly 28 in a position wherein trigger 22 will be effective in activating the device. This position is illustrated in FIGS. 4 and 5 of the drawings. The patient will depress trigger 22 which will then release tabs 54 and 58 on legs 52 and 56 respectively. This permits springs 44 to drive plunger rod 60 against plunger 76. This results in first piercing tip 68 extending outwardly of the outer housing while also causing second piercing tip to pierce pierceable top 80 of cartridge 74. The medicine is then injected into the patient.

Subsequently, after injection, spring 112 will cause upward movement of the needle hub 64 and vial to thereby store the needle within the auto-injector.

We claim:
1. An auto-injector (10) comprising:
an outer housing (12, 14) having a proximal end (18) and a distal end (16);

an inner housing (84), a cartridge (74) located within said inner housing (84), said cartridge (74) containing a medicament, said cartridge (74) having one end thereof sealed by a pierceable member (80);

a needle hub (64), said needle hub (64) having first and second piercing tips (68, 70), said first and second piercing tips being in fluid communication;

an actuating assembly (28), said actuating assembly (28) being arranged to move an actuator from a first storage position to an activated position wherein said first piercing tip (68) extends outwardly of said outer housing (12, 14) at said proximal end (18) and said second piercing tip (70) pierces said pierceable member (80);

a first trigger (22) being located at said distal end (16), a second trigger (98) being located at said proximal end (18), said first trigger (22) being spaced from said actuating assembly (28) such that depression of said first trigger (22) does not activate said actuating assembly (28), said second trigger (98), upon being activated, causes said actuating assembly (28) to move to then permit said first trigger (22) to activate said actuating assembly (28), said actuating assembly (28) comprising an upper member (30) and a lower member (32), said lower member (32) having first and second upwardly extending elements (52, 54), said upwardly extending elements (52, 54) locking with said upper member, first and second compressed springs (44) extending between said lower member (32) and said upper member (30), said first trigger (22) being operative to unlock said upwardly extending elements (52, 54) from said upper member, said cartridge having a cap (80) forming said pierceable member, a plunger (76) within said cartridge, said actuating assembly (28) including a plunger rod (60), said plunger rod (60) engaging said plunger (76) to cause said first piercing tip (68) to extend outwardly of said outer housing and said second piercing tip (70) to pierce said cap (80) of said cartridge, said first compressed spring extending around said first upwardly extending element, and said second compressed spring extending around said second upwardly extending element.

2. The auto-injector of claim 1 further including a spring (34) biasing said first trigger (22).

3. The auto-injector of claim 1 wherein said second trigger (98) is activated by pressing the auto-injector against a resilient surface.

4. The auto-injector of claim 1 further including a cover (126) for said proximal end.

5. The auto-injector of claim 4 further including a printed circuit board (26) and a battery (24) mounted within said outer housing (12, 14) at said distal end configured to send a signal when said auto-injector has been activated.

6. The auto-injector of claim 5 further including a spring (112) biasing said needle hub (64) to a retracted position after deployment thereof.

7. The auto-injector of claim 1 further including a detector (29) for detecting activation of the auto-injector.

8. The auto-injector of claim 7 wherein said detector comprises first and second contacts (29), said contacts being held in a normally spaced relationship, said contacts contacting each other following activation of the actuation assembly.

* * * * *